United States Patent [19]
Hwang et al.

[11] Patent Number: 5,416,077
[45] Date of Patent: May 16, 1995

[54] PHYSICAL STABILITY IMPROVEMENT OF LIQUID NUTRITIONAL PRODUCTS

[75] Inventors: Shie-Ming Hwang, Columbus; Timothy W. Schenz, Powell; James N. Chmura, Pickerington, all of Ohio

[73] Assignee: Abbott Laboratories, Abbott Park, Ill.

[21] Appl. No.: 246,587

[22] Filed: May 20, 1994

Related U.S. Application Data

[63] Continuation of Ser. No. 933,630, Aug. 24, 1992, abandoned, which is a continuation of Ser. No. 596,140, Oct. 10, 1990, abandoned.

[51] Int. Cl.$^6$ ............... C08B 37/00; A23L 1/0532
[52] U.S. Cl. .............................. 514/54; 536/52; 536/114; 424/439; 426/520; 426/654; 426/658
[58] Field of Search ............... 514/54; 536/52, 114; 424/439; 426/520, 654, 658

[56] References Cited

U.S. PATENT DOCUMENTS

| | | | |
|---|---|---|---|
| 3,544,333 | 12/1970 | Glabe et al. | 426/557 |
| 4,242,367 | 12/1980 | Igoe | 426/573 |
| 4,282,262 | 8/1981 | Blake | 426/565 |
| 4,389,426 | 6/1983 | Reissmann et al. | 426/602 |
| 4,427,704 | 1/1984 | Cheney et al. | 426/104 |
| 4,479,973 | 10/1984 | Holley | 426/573 |
| 4,609,554 | 9/1986 | Barua et al. | 426/43 |
| 4,623,552 | 11/1986 | Rapp | 426/575 |
| 4,684,533 | 8/1987 | Kratochvil | 426/575 |
| 4,748,026 | 5/1988 | Keefer et al. | 426/43 |
| 5,002,934 | 3/1991 | Norton et al. | 514/54 |

FOREIGN PATENT DOCUMENTS 1220838  5/1968  United Kingdom .
1220696  7/1968  United Kingdom .

OTHER PUBLICATIONS

Mankes et al.; Chemical Abstracts 83:204560f (1975).
*The Merck Index;* 10th edition; editor M. Windholz Publ. Merck & Co., Inc. p. 260 item 1848 (1987).
Mochida et al.; Chemical Abstracts 108:62439g (1988).
Saisu; Chemical Abstracts 110:191537c (1989) (May).
Coste et al.; Chemical Abstracts 110:211169q (Jun. 1989).
Nakamura et al.; Chemical Abstracts 112:215499m (Jun. 1990).

*Primary Examiner*—Douglas W. Robinson
*Assistant Examiner*—Kathleen Kahler Fonda
*Attorney, Agent, or Firm*—Donald O. Nickol; Lonnie R. Drayer

[57] ABSTRACT

There is disclosed liquid nutritionals with improved physical stability. The nutritionals are pourable yet able to hold minerals in suspension without sedimentation or sag. The invention comprises the use of iota-carrageenan of a concentration of between 50–1500 parts per million. The nutritional may also comprise kappa carrageenan at a concentration of less than 25% of the total concentration of iota- and kappa-carrageenan. There is further disclosed a method for preparing the liquid nutritional through the use of ultra-high temperature heat treatment.

21 Claims, No Drawings

PHYSICAL STABILITY IMPROVEMENT OF LIQUID NUTRITIONAL PRODUCTS

This is a continuation of application Ser. No. 07/933,630 filed Aug. 24, 1992, now abandoned, which is a continuation of application Ser. No. 07/596,140 filed on Oct. 10, 1990, now abandoned.

TECHNICAL FIELD

The present invention relates generally to liquid nutritionals, and more particularly, to a physical stability improvement for use in liquid nutritional products.

BACKGROUND ART

The liquid nutritional industry is a multi-billion dollar a year business. Two of the major components of the industry are infant formula and medical nutritionals. These types of liquid nutritionals contain an appreciable amount of minerals suspended in a liquid medium. The presence of these minerals is vitally important to the efficacy of the liquid nutritionals, however, the presence of the minerals and high levels of protein and fat causes a number of problems.

For decades, the usage and marketing of liquid nutritionals traditionally have been confronted with two major problems. The first problem is known as creaming, whereby the fat globules in the liquid nutritional float to the top of the product. A problem can arise if these fat globules harden, effectively forming a seal across the top of the liquid nutritional's container. Additionally these hard, fatty deposits can block or clog feeding tubes or nipples.

The second problem associated with liquid nutritionals is sedimentation, whereby minerals come out of solution and settle to the bottom of the product container. The problem of sedimentation is made more acute where the sediment hardens into a cementous type of material known as "nondispersible sediment". The problem with nondispersible sediment is two-fold. First, the liquid nutritional is now subject to nutrient deficiency, since the nondispersible sediment often refuses to go back into solution upon the shaking of the container. The second problem with nondispersible sediment is that it, along with hardened creaming deposits, can plug feeding tubes or nipples.

Modified stabilizer systems have been proposed to address the sediment problem, however, they have met with limited success. These systems permit the minerals to be suspended longer, but nevertheless they ultimately fall from solution. In this modified system iota-carrageenan is combined with kappa-carrageenan in a ratio of 2:1. However, a new problem exists with such modified systems. The phenomenon known as "sag" occurs in these stabilizer systems as the components of the liquid nutritional flocculate and separate over time. "Sag" is a separation of the product matrix in which flocculent and clear areas develop. The resultant liquid nutritional looks "curdled" or the victim of bacterial spoilage. Another alternative solution to the problem of the physical stability of liquid nutritional products is the micronization of the salts or minerals in the liquid nutritional. This approach is costly, and any creaming or sedimentation which occurs is typically not able to be disposed of by shaking the container.

Still another approach to the problem involves the use of soluble calcium in an attempt to avoid problems with the calcium minerals coming out of solution. However, the problem caused by creaming remains and potential plugging of the feeding tubes or nipples is still a possibility.

Obvious problems exist in the marketing of the liquid nutritionals discussed above inasmuch as consumers are reluctant to buy product that appears to be spoiled, even if in point of fact there is nothing nutritionally wrong with the product. Heretofore, this problem has been addressed by the packaging of liquid nutritionals in cans or opaque containers which do not permit the consumer to visually inspect the product prior to use.

One of the key components of liquid nutritionals with respect to product stability is carrageenan. Carrageenan is a group of highly sulfated high molecular weight linear polysaccharides. The functionality of carrageenan can be attributed to its chemical structure, especially the ester sulfate group content and molecular size. There are three main types of carrageenan: kappa, lambda, and iota.

When heated in water, dissolved carrageenan molecules exist as random coils. Upon cooling and in the presence of appropriate cations, kappa and iota carrageenan molecules form double helix domains and aggregate to form gels of different textures. Kappa carrageenan forms a strong rigid gel through ion-bridging between negatively charged sulfate groups. Iota carrageenan forms elastic gels in the presence of calcium ions due to the higher sulfate group content which imposes higher electrostatic repulsive force and keeps molecules and helices from getting too close to form a tight and rigid gel. Lambda carrageenan will not gel because of the high sulfate group content and corresponding strong repulsive force which keeps molecules from forming double helices and gel.

Carrageenan has heretofore been used as a thickening agent in the food industry, for such products as cheese, mayonnaise, pudding, frozen dairy desserts, and pet food. The use of carrageenan in connection with solid food products is disclosed in U.S. Pat. Nos. 4,427,704; 4,623,552; 4,282,262; 3,544,333; 4,389,426; 4,609,554; 4,684,533; 4,748,026; and 4,479,973.

The use of a mixture or a reaction product of at least one carrageenan and at least one glucomannan in foods products, and especially as part of a gelling systems for use in the preparation of gelled or thickened food products is disclosed in U.S. Pat. No. 4,427,704 to Cheney et al. Although the carrageenan is disclosed as being any form of carrageenan or a mixture thereof, the preferred carrageenan types contain some kappa-carrageenan.

The use of kappa-carrageenan, iota-carrageenan and mixtures thereof in a pudding composition is disclosed in U.S. Pat. No. 4,623,552 to Rapp. Typically the total carrageenan content is in the range of from about 0.05% to about 1.0% by weight; preferably from about 0.1% to about 0.5%, and most preferably from about 0.1% to about 0.3% by weight. In the three examples illustrating the U.S. Pat. No. 4,623,552 invention, kappa-carrageenan is used exclusively or in greater concentrations than are associated with iota-carrageenan.

The use of carrageenan as a stabilizer gum in a dairy based dessert mix composition, which upon aeration can be statically frozen to provide aerated frozen desserts, is disclosed in U.S. Pat. No. 4,282,262 to Blake. The only specific type of carrageenan mentioned is kappa-carrageenan.

The use of iota-carrageenan in the preparation of a nonfat milk macaroni product is disclosed in U.S Pat. No. 3,544,333 to Glabe et al. Preferably the iota-carrageenan content is in the range of from about 0.01% to 0.2% by weight.

The use of a gelling system for a low-fat spread comprising at least one hydrocolloid capable of forming a linear gel structure such as lambda-carrageenan, and at least one other hydrocolloid capable of forming a spherical gel structure such as iota-carrageenan, is disclosed in U.S. Pat. No. 4,389,426 to Reissmann et al. Other suitable hydrocolloids are also mentioned.

The use of carrageenan as a thickener in aseptic yogurt is disclosed in U.S. Pat. No. 4,609,554. The concentration of the carrageenan is in the range of from about 0.1% to 0.8%. Heating of the mixture after introduction of the carrageenan yet prior to pasteurization preferably occurs, with such heating being up to a temperature of about 160° F.

The use of carrageenan, specifically kappa-carrageenan, of from about 0.5% to about 3.0% by weight along with fat, gelatin and water in an imitation cheese product is disclosed in U.S. Pat. No. 4,684,533 to Kratochvil. The gelatin and kappa-carrageenan are present as a structurally firm continuous aqueous carrageenan/gelatin phase matrix at refrigeration temperatures.

The use of carrageenan in a process for production of a no-starch shelf stable yogurt product is disclosed in U.S. Pat. No. 4,748,026 to Keefer et al. The preferred weight range of the carrageenan is about 0.05% to about 3.0% by weight. The carrageenan in this invention serves as a calcium binder to inhibit curd formation in the yogurt.

The use of iota-carrageenan in a gelled milk composition, such as gelled milk desserts, is disclosed in U.S. Pat. No. 4,479,973 to Holley. The invention utilizes ultra high temperature processing. The concentration of the iota-carrageenan is in the range of about 0.15% to about 0.5% by weight.

As the above patents disclose, the carrageenan most widely and often used in the food industry is kappa carrageenan. However, while kappa-carrageenan is an effective stabilizer in connection with solid food, it must be recognized that sedimentation, sag and creaming are not nearly as much a problem in solid foods as they are in liquid nutritionals.

It is thus apparent that a need exists for a physical stability improvement in liquid nutritional products which provides an extremely shelf-stable liquid nutritional with minimal problems from sag, sedimentation, and creaming. While the liquid nutritional of this invention is particularly suited for infant formulas and medical nutritionals, it is contemplated herein that the invention would be useful for any liquid nutritional that heretofore has encountered the problems of sag, sedimentation, or creaming.

DISCLOSURE OF THE INVENTION

There is disclosed a liquid nutritional with improved physical stability, said liquid nutritional comprising iota-carrageenan of a concentration of between 50–1500 parts per million, said concentration being low enough for said nutritional to be pourable, yet said concentration being high enough to hold minerals in suspension with minimum sedimentation. Preferably the nutritional also comprises kappa carrageenan, said kappa carrageenan being at a concentration of less than 25% of the total concentration of iota and kappa carrageenan. Additionally, the nutritional is preferably subjected to ultra high temperature heat treatment for stabilizing purposes.

Preferable concentrations of iota-carrageenan are between 800–1000 parts per million, and more particularly between 800–900 parts per million, as well as between 250–450 parts per million and more particularly between 300–350 parts per million.

There is also disclosed a liquid nutritional with improved physical stability, said liquid nutritional comprising iota-carrageenan and kappa-carrageenan in a ratio of iota-carrageenan to kappa-carrageenan of at least 3:1, said iota-carrageenan being of a concentration of between 50–1500 parts per million, said nutritional being pourable, and said nutritional being substantially devoid of sedimentation. Additionally, the nutritional is substantially devoid of creaming and sag. Furthermore, the nutritional is subjected to ultra-high temperature heat treatment for stabilizing purposes.

There is further disclosed a method for preparing a liquid nutritional with improved physical stability comprising the steps of mixing the ingredients of said nutritional, said nutritional comprising iota-carrageenan at a concentration of between 50–1500 parts per million, said concentration being low enough for said nutritional to be pourable, yet said concentration being high enough to hold minerals in suspension without sedimentation; subjecting said nutritional to ultra-high temperature heat treatment; cooling said nutritional; packaging said nutritional; and sterilizing said packaged nutritional.

Preferably the liquid nutritional made in accordance with this method also comprises kappa-carrageenan, said concentration of iota-carrageenan exceeding the concentration of kappa-carrageenan in said nutritional by a ratio of at least 3:1. Preferably the concentration of iota-carrageenan is between 800–900 parts per million or between 250–450 parts per million, and even more preferably between 300–350 parts per million depending on the product matrix.

One aspect of the present invention provides for a liquid nutritional with improved physical stability, that is a liquid nutritional which experiences minimal sedimentation, creaming or sag.

Another aspect of the invention provides a product possessing a yield stress (the stress above which flow begins) which exceeds approximately 0.1–1.0 dyne per square centimeter. Yield stress refers to a minimum sheer stress or force that must be applied to the fluid to initiate flow deformation. Examples of materials having a yield stress are ketchup, mustard, toothpaste, mayonnaise and various polymer solutions.

Yet another aspect of the invention resides in a liquid nutritional which is quite shear-thinning such that the product is freely flowing at shear rates at which the product is poured or consumed.

Yet another aspect of the invention resides in the formation of a weak three-dimensional network through interaction of the carrageenan and the liquid nutritional in order to maintain product emulsion and suspension stability.

Substantial effort to solve the problems encountered in medical nutritional has been expended by the industry. The problems encountered by medical nutritionals are unique since other foods, either liquid or solid (i.e. yogurt), are not required to deliver all or a substantial portion of the vitamins, minerals, protein and the like for the average adult or infant. Thus, a solution to the problems would fulfill a long felt need in a very specific industry.

Other aspects and advantages of the instant invention will be apparent from the following description, examples, and the appended claims.

DETAILED DESCRIPTION OF THE INVENTION

Specifically, the present invention is concerned with a liquid nutritional with improved physical stability. Most conventional sol id nutritionals favor the utilization of kappa-carrageenan either alone or in combination with lower levels of iota- and/or lambda-carrageenan. Conventional liquid nutritionals have previously utilized kappa-carrageenan or modified stabilization systems which include no more than 66% iota-carrageenan. As a result of the inventors' endeavors it has been discovered that superior results can be achieved when the liquid nutritional contains mostly, if not solely, iota-carrageenan. If kappa-carrageenan is present, then the ratio of iota-carrageenan to kappa-carrageenan must be greater than or equal to a ratio of 3:1.

The type of iota-carrageenan used in this invention is represented by VISCARIN ® SA-359 (FMC Corporation), a relatively weak gelling iota-carrageenan. The type of kappa-carrageenan used in this invention is represented by SEAKEM ® CM-514 (FMC Corporation), which contains a weak gelling kappa-carrageenan, a non-gelling lambda-carrageenan, and dextrose. Those skilled in this art will appreciate that numerous suppliers can provide the various forms of the carrageenan and that they would be suitable for use in the present invention.

It has been discovered that the utilization of greater concentrations of carrageenan than have previously been used in connection with stabilization systems in liquid nutritionals, and more particularly such concentrations that include solely or primarily iota-carrageenan results in the formation of what is believed to be a weak three-dimensional network which effectively holds the minerals as well as fat globules in the matrix of the nutritional. By holding the minerals in this weak three-dimensional network, the result is no sedimentation or sagging. By holding the fat globules in the weak three-dimensional network, the result is no creaming.

The specific concentrations of the iota-carrageenan may range from 50–1500 parts per million depending on the type and nature of the product matrix. Nevertheless, certain rheological properties are attendant to the liquid nutritional produced by this invention. For example, the product possesses a yield stress (a stress above which flow begins) such that the yield stress exceeds about 0.1 dyne per square centimeter, preferably about 1.0 dyne per square centimeter. Furthermore, the desired rheology allows the liquid to be quite shear-thinning, such that it is freely flowing at shear rates at which the product is poured or consumed.

It has also been discovered that although the selection of iota-carrageenan concentration is product matrix dependent, further improved results can be obtained when the product is subjected to ultra high temperatures for a short time, a form of heat treatment, traditionally used to kill spores, as opposed to being used for purposes related to the stabilization of a liquid nutritional. The heat treatment associated with this invention occurs by heating the pipeline through which the liquid nutritional passes. Once the liquid nutritional passes the area of the pipeline which has been heated, the liquid nutritional is then passed through a homogenizer and cooled within the line such that when the liquid nutritional is subsequently bottled and then sterilized, no sag or gel aggregates form over the course of time.

In actual use, the invention is product matrix dependent, so the specific amount of iota-carrageenan present varies from product to product. Although the addition of 50–1500 parts per million is claimed to be part of the invention, specific acceptable ranges for two specific products have been determined.

BEST MODE FOR CARRYING OUT THE INVENTION

For example, the use of between 300–350 parts per million of iota-carrageenan from the carrageenan commodity known as VISCARIN ® SA-359, (a relatively weak gelling iota-carrageenan) in the formulation of vanilla ENSURE PLUS ® (high calorie liquid nutritional, Ross Laboratories Division of Abbott Laboratories) results in a product exhibiting improved physical stability. This is especially apparent when the product is subjected to a short ultra-high temperature treatment which results in a liquid nutritional essentially devoid of sedimentation and sag. For purposes of this disclosure, an ultra-high temperature (or UHT) treatment or process is one in which the product is heated to a temperature of 130°–160° C. in continuous flow in a heat exchanger and held at that temperature for a sufficient length of time to produce a satisfactory level of commercial sterility with an acceptable amount of change in the product. Those skilled in the art will readily appreciate what UHT is and how it is employed. For further explanation see Burton, H., *Ultra-High-Temperature Processing of Milk and Milk Products,* Elsevier Applied Science, New York and London, 1988.

Additionally, another liquid nutritional with improved physical stability was produced via the addition of 800–900 parts per million of VISCARIN ® SA-359 to INTROLITE ™ (a liquid nutritional of Ross Laboratories Division of Abbott Laboratories). Product stability was further enhanced when the liquid nutritional was subjected to UHT. The product was essentially devoid of sedimentation and sag.

The invention will be better understood in view of the following examples, which are illustrative only and should not be construed as limiting the invention.

EXPERIMENTAL

The concept of the present invention was tested in two commercially available liquid nutritional formulations. The first was Introl ™, a fortified half-calorie liquid nutritional (Ross Laboratories Division of Abbott Laboratories). Introlite ™ is a liquid food for introductory tube feeding and contains 700 calories in 1321 ml and meets 100% of the U.S. RDA for vitamins and minerals. The second was Ensure Plus ®, a high calorie liquid-nutritional providing complete balanced nutrition (Ross Laboratories Division of Abbott Laboratories). Ensure Plus ® contains 1500 calories per liters with a caloric distribution of 14.7% protein, 32% fat and 53.3% carbohydrate.

The actual compositions and methods of preparation are standard in the industry. In general, slurries of carbohydrate and minerals; protein and fat; and protein and water are prepared and then blended. In actual production, the slurries are blended, heated, deaerated, homogenized, sterilized and packaged.

In the following examples, the only variables were the type and amount of carrageenan and the presence or absence of UHT. After each specific formula was prepared (control or invention) at least five 8-ounce (0.23 kg) glass bottles and/or ready-to-hang plastic containers were filled with product and then thermally sterilized. These glass bottles and/or plastic containers were then allowed to stand at room temperature to evaluate the effectiveness of the invention.

EXAMPLE 1—Control

Commercially available Introlite ™ liquid nutritional contains approximately 720 parts per million of carrageenan and is 11.88% solids by weight. The composition comprises essentially 240 parts per million of kappa-carrageenan and 480 ppm iota-carrageenan. Noticeable sag occurs within 2 to 7 days. Additionally, after four months of time the cream layer measured 3.0 mm and the sediment layer measures 2.5 mm.

EXAMPLE 2—Control

When the concentration of kappa-carrageenan is lowered to 35 parts per million in Introlite ™ noticeable sedimentation occurred within 1–3 weeks and creaming occurred within 3–6 months.

EXAMPLE 3—Control

To the formula of the liquid nutritional of Example 1, additional kappa-carrageenan was added. When the total amount of carrageenan exceeds a concentration of 1000 parts per million (ie. 480 parts per million iota-carrageenan and at least 520 parts per million kappa-carrageenan) the nutritional became gelatinous within 3–6 months and hence no longer useful as a liquid nutritional.

EXAMPLE 4—Control

The formula of Example 1 was tested except the concentration of kappa-carrageenan was lowered to 60 parts per million while the concentration of iota-carrageenan remained at 480 parts per million. The resultant formula exhibited slight sedimentation and sag within about 1–3 weeks.

EXAMPLE 5—Control

The formula of Example 1 was tested except that the concentration of kappa-carrageenan was lowered to 193 parts per million while the concentration of iota-carrageenan was lowered to 387 parts per million. The ratio of iota-carrageenan to kappa-carrageenan was still approximately 2:1. The resultant formula exhibited sag and sedimentation within 1–3 weeks.

EXAMPLE 6—Invention

The formula of Example 1 was used except the concentration of iota-carrageenan was raised to 740 parts per million and the concentration of kappa-carrageenan was lowered to 60 parts per million. After four months, very little sedimentation (0.5 mm) was noticeable, although minor creaming (2.0 mm) did occur.

EXAMPLE 7—Invention

The formula of Example 1 was used except the concentration of iota-carrageenan was raised to 800 parts per million and the concentration of kappa-carrageenan was lowered to essentially 0 parts per million. No sedimentation, creaming or sag was noticeable after 12 months of storage at room-temperature.

EXAMPLE 8—Invention

The formula of Example 1 was used except the concentration of total carrageenan was raised to 900 parts per million, with the ratio of iota-carrageenan to kappa-carrageenan being approximately 3:1. A slight sag which was acceptable was present after 1 month. No sedimentation or creaming were noticeable after 12 months of storage at room temperature.

EXAMPLE 9—Invention

The formula of Example 1 was used except the concentration of iota-carrageenan was raised to 900 parts per million and the concentration of kappa-carrageenan was lowered to essentially 0 parts per million. No sedimentation, creaming or sag are noticeable after 12 months of storage.

EXAMPLE 10—Control

The formula of Example 1 was used except the concentration of total carrageenan was raised to 1000 parts per million. Although there was no sag or sedimentation, there is a viscosity problem, such that the liquid nutritional was difficult to pour within 1–2 months of storage.

EXAMPLE 11—Control

Ensue Plus ® is a commercially available liquid nutritional which contains approximately 225 parts per million of carrageenan and is about 30% solids by weight. The composition comprises essentially 225 parts per million of kappa-carrageenan and noticeable sag occurs within 1–3 weeks.

EXAMPLE 12—Control

The formula of Example 11 was used except the concentration of kappa-carrageenan was lowered to 35 parts per million. Noticeable sedimentation and creaming occurred within 1–3 months.

EXAMPLE 13—Control

The formula of Example 11 was used except the concentration of kappa-carrageenan was lowered to 75 parts per million while the concentration of iota-carrageenan was raised to 150 ppm. Sagging occurred within 1–3 weeks.

EXAMPLE 14—Invention

The formula of Example 11 was used except the concentration of kappa-carrageenan was lowered to approximately 0 parts per million, while the concentration of iota-carrageenan was raised to 225 parts per million. The product was subjected to UHT. No sagging occurred, however, noticeable sedimentation did occur within 1–2 months.

EXAMPLE 15—Control

The formula of Example 11 was used except the concentration of kappa-carrageenan was lowered to 75 parts per million, while the concentration of iota-carrageenan was raised to 150 parts per million. The product was subjected to UHT. While no sagging occurred, sedimentation did occur within 1–2 months.

EXAMPLE 16—Invention

The formula of Example 11 was used except the concentration of kappa-carrageenan was lowered to approximately 0 parts per million, while the concentration of iota-carrageenan was raised to 300 parts per million. Little or no sagging or sedimentation occurred after 8 months of storage at room temperature.

EXAMPLE 17—Control

The formula of Example 11 was used except the concentration of kappa-carrageenan was lowered to 125 parts per million, while the concentration of iota-carrageenan was raised to 250 parts per million. While no sedimentation occurred, very slight sagging did occur with 1–2 months.

EXAMPLE 18—Invention

The formula of Example 7 was bottled, then subjected to sterilization. Afterwards, there was no evidence of sag after 12 months.

EXAMPLE 19—Control

The formula of Example 7 was used except kappa-carrageenan was substituted for the iota-carrageenan. The formula was bottled, then subjected to sterilization. A diagonal sag line became visible from the top to the bottom of the container within 1–3 weeks.

EXAMPLE 20—Invention

The formula of Example 6 was bottled and subjected to sterilization. Very little sedimentation was noticeable after 12 months of storage at room temperature.

EXAMPLE 21—Invention

The formula of Example 6 is passed through UHT, then cooled, bottled and sterilized. Less sag and sedimentation were present than in Example 20 after 12 months.

INDUSTRIAL APPLICABILITY

The data demonstrate that the liquid nutritional prepared in accordance with this invention possesses improved physical stability with respect to creaming, sedimentation, and sag. The problems encountered by the medical and infant nutritional industry in preparing products that exhibit good shelf life (product stability) are unique. Due to the high loadings of minerals and vitamins found in these products and the high viscosities, the nutritional industry, until now, has failed to provide a solution to this long felt need. Through the discoveries disclosed in this invention the nutritional industry can prepare and supply liquid nutritional products that do not suffer from the problems of sag, sedimentation, or creaming.

While the liquid nutritional herein described and the method of making same constitute preferred embodiments of the invention, it is to be understood that the invention is not limited to this precise formulation and that changes may be made therein without departing from the scope of the invention which is defined in the appended claims.

What is claimed is:

1. A liquid nutritional composition comprising:
   (a) a liquid nutritional mixture containing fat globules present at a concentration sufficient to have said liquid nutritional mixture be susceptible to creaming, containing suspended minerals, and containing total solids, including said suspended minerals, in the range of from about 11.88% to about 30% by weight; and
   (b) iota-carrageenan present in said liquid nutritional composition at a concentration in the range of 50 to 1000 parts per million, wherein said liquid nutritional composition is essentially devoid of creaming, sagging, and sedimentation.

2. A liquid nutritional composition according to claim 1, wherein said liquid nutritional composition further comprises kappa-carrageenan, said kappa-carrageenan present at a concentration less than 25% of the total concentration of said iota-carrageenan and said kappa-carrageenan.

3. A liquid nutritional composition according to claim 1 wherein said concentration of said iota-carrageenan is in the range of 800 to 900 parts per million.

4. A liquid nutritional composition according to claim 1 wherein said concentration of said iota-carrageenan is in the range of 250 to 450 parts per million.

5. A liquid nutritional composition according to claim 4 wherein said concentration of said iota-carrageenan is in the range of 300 to 350 parts per million.

6. A liquid nutritional composition according to claim 2 wherein said concentration of said iota-carrageenan is in the range of 800 to 900 parts per million.

7. A liquid nutritional composition according to claim 2 wherein said concentration of said iota-carrageenan is in the range of 250 to 450 parts per million.

8. A liquid nutritional composition according to claim 7 wherein said concentration of said iota-carrageenan is in the range of 300 to 350 parts per million.

9. A method of preparing a liquid nutritional composition, said method comprising the steps of:
   (a) preparing a mixture comprising:
      (i) a liquid nutritional mixture containing fat globules present at a concentration sufficient to have said liquid nutritional mixture be susceptible to creaming, containing minerals, and containing total solids, including said suspended minerals, in the range of from about 11.88% to about 30% by weight; and
      (ii) iota-carrageenan present in said liquid nutritional composition at a concentration in the range of 50 to 1000 parts per million;
   (b) subjecting the said liquid nutritional composition resulting from step (a) to ultra high temperature; followed by
   (c) cooling said liquid nutritional composition from said ultra high temperature; and
   (d) packaging said liquid nutritional composition, wherein said liquid nutritional composition is essentially devoid of creaming, sagging, and sedimentation.

10. A method according to claim 9, wherein said liquid nutritional composition further comprises kappa-carrageenan, said kappa-carrageenan present at a concentration less than 25% of the total concentration of said iota-carrageenan and said kappa-carrageenan.

11. A method according to claim 9 wherein said concentration of said iota-carrageenan is in the range of 800 to 900 parts per million.

12. A method according to claim 9 wherein said concentration of said iota-carrageenan is in the range of 250 to 450 parts per million.

13. A method according to claim 12 wherein said concentration of said iota-carrageenan is in the range of 300 to 350 parts per million.

14. A method according to claim 10 wherein said concentration of said iota-carrageenan is in the range of 800 to 900 parts per million.

15. A method according to claim 10 wherein said concentration of said iota-carrageenan is in the range of 250 to 450 parts per million.

16. A method according to claim 15 wherein said concentration of said iota-carrageenan is in the range of 300 to 350 parts per million.

17. A liquid nutritional composition according to claim 1 wherein said fat globules are present at a concentration of about 32% by weight.

18. A liquid nutritional composition according to claim 1 wherein said liquid nutritional composition has a caloric content in the range of from about 530 calories per liter to about 1,500 calories per liter.

19. A liquid nutritional composition according to claim 1 wherein said liquid nutritional composition has a caloric distribution of about 14.7% protein, 32% fat, and 53.3% carbohydrate.

20. A liquid nutritional composition comprising:
  (a) a liquid nutritional mixture containing fat globules present at a concentration sufficient to have said liquid nutritional mixture be susceptible to creaming, containing suspended minerals, containing total solids, including said suspended minerals, in the range of from about 11.88% to about 30% by weight, and having a caloric content from about 530 to about 1,500 calories per liter; and
  (b) iota-carrageenan present in said liquid nutritional composition at a concentration in the range of 50 to 1000 pans per million, wherein said liquid nutritional composition is essentially devoid of creaming, sagging, and sedimentation.

21. A liquid nutritional composition comprising:
  (a) a liquid nutritional mixture containing fat globules present at a concentration sufficient to have said liquid nutritional mixture be susceptible to creaming, containing suspended minerals, containing total solids, including said suspended minerals, in the range of from about 11.88% to about 30% by weight, having a caloric content from about 530 to about 1,500 calories per liter, and having a caloric distribution of 14.7% protein, 32% fat, and 53.3% carbohydrate; and
  (b) iota-carrageenan present in said liquid nutritional composition at a concentration in the range of 50 to 1000 parts per million, wherein said liquid nutritional composition is essentially devoid of creaming, sagging, and sedimentation.

* * * * *